(12) United States Patent
Haddach et al.

(10) Patent No.: US 6,440,960 B1
(45) Date of Patent: Aug. 27, 2002

(54) CRF RECEPTOR ANTAGONISTS AND METHODS RELATING THERETO

(75) Inventors: Mustapha Haddach; John Patrick Williams, both of San Diego; Dragan Marinkovic, Del Mar; Jane Han Bu, San Diego, all of CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 14 days.

(21) Appl. No.: 09/861,195

(22) Filed: May 18, 2001

Related U.S. Application Data

(60) Provisional application No. 60/205,607, filed on May 18, 2000, provisional application No. 60/205,611, filed on May 18, 2000, and provisional application No. 60/205,614, filed on May 18, 2000.

(51) Int. Cl.[7] .................... C07D 498/16; C07D 513/16; A61K 31/535; A61K 31/4162
(52) U.S. Cl. ................. 514/224.5; 514/230.2; 514/267; 514/293; 544/34; 544/101; 544/250; 544/251; 546/83
(58) Field of Search .......................... 544/34, 101, 250, 544/251; 546/83; 514/224.5, 230.2, 267, 293

(56) References Cited

FOREIGN PATENT DOCUMENTS

| WO | WO 97/44038 | 11/1997 |
|---|---|---|
| WO | WO 98/08847 | 3/1998 |
| WO | WO 99/40091 | 8/1999 |
| WO | WO 00/27846 | 5/2000 |

OTHER PUBLICATIONS

Skaric et al., Novel [1,4]thiazino[4,3,2–gh]purines from allyl–hypoxanthine derivatives, Vestn. Slov. Kem. Drus., 33(3), pp. 305–323, 1986.*
Bodell, "Investigation of 6–Thiodeoxyguanosine Alkylation Products and Their Role in the Potentiation of BCNU Cytotoxicity," Chemical Abstracts 106(21):170733, May 25, 1987.

* cited by examiner

Primary Examiner—Deepak R. Rao
(74) Attorney, Agent, or Firm—Seed Intellectual Property Law Group PLLC

(57) ABSTRACT

CRF receptor antagonists are disclosed which have utility in the treatment of a variety of disorders, including the treatment of disorders manifesting hypersecretion of CRF in a warm-blooded animals, such as stroke. The CRF receptor antagonists of this invention have the following structure:

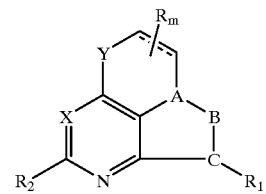

including stereoisomers, prodrugs and pharmaceutically acceptable salts thereof, wherein m, R, $R_1$, $R_2$, X, Y, A, B and C are as defined herein. Compositions containing a CRF receptor antagonist in combination with a pharmaceutically acceptable carrier are also disclosed, as well as methods for use of the same

22 Claims, No Drawings

CRF RECEPTOR ANTAGONISTS AND METHODS RELATING THERETO

CROSS REFERENCE TO RELATED APPLICATIONS

This application claims the benefit of U.S. Provisional Application No. 60/205,607 filed May 18, 2000, U.S. Provisional Application No. 60/205,611 filed May 18, 2000 and U.S. Provisional Application No. 60/205,614 filed May 18, 2000.

TECHNICAL FIELD

This invention relates generally to CRF receptor antagonists, and to methods of treating disorders by administration of such antagonists to a warm-blooded animal in need thereof.

BACKGROUND OF THE INVENTION

The first corticotropin-releasing factor (CRF) was isolated from ovine hypothalmi and identified as a 41-amino acid peptide (Vale et al., Science 213:1394–1397, 1981). Subsequently, sequences of human and rat CRF were isolated and determined to be identical, but different from ovine CRF in 7 of the 41 amino acid residues (Rivier et al., Proc. Natl. Acad. Sci. USA 80:4851, 1983; Shibahara et al., EMBO J. 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., Science 213:1394–1397, 1981). Briefly, CRF is believed to initiate its biological effects by binding to a plasma membrane receptor which has been found to be distributed throughout the brain (DeSouza et al., Science 224:1449–1451, 1984), pituitary (DeSouza et al., Methods Enzymol. 124:560, 1986; Wynn et al., Biochem. Biophys. Res. Comm. 110:602–608, 1983), adrenals (Udelsman et al., Nature 319:147–150, 1986) and spleen (Webster, E. L., and E. B. DeSouza, Endocrinology 122:609–617, 1988). The CRF receptor is coupled to a GTP-binding protein (Perrin et al., Endocrinology 118:1171–1179, 1986) which mediates CRF-stimulated increase in intracellular production of cAMP (Bilezikjian, L. M., and W. W. Vale, Endocrinology 113:657–662, 1983). The receptor for CRF has now been cloned from rat (Perrin et al., Endo 133(6):3058–3061, 1993), and human brain (Chen et al., PNAS 90(19):8967–8971, 1993; Vita et al., FEBS 335(1):1–5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., J. Clin. Invest. 90:2555–2564, 1992; Sapolsky et al., Science 238:522–524, 1987; Tilders et al., Regul. Peptides 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., Nature 297:331, 1982), persistent activation of the electroencephalogram (Ehlers et al., Brain Res. 278:332, 1983), stimulation of the sympathoadrenomedullary pathway (Brown et al., Endocrinology 110:928, 1982), an increase of heart rate and blood pressure (Fisher et al., Endocrinology 110:2222, 1982), an increase in oxygen consumption (Brown et al., Life Sciences 30:207, 1982), alteration of gastrointestinal activity (Williams et al., Am. J. Physiol. 253:G582, 1987), suppression of food consumption (Levine et al., Neuropharmacology 22:337, 1983), modification of sexual behavior (Sirinathsinghji et al., Nature 305:232, 1983), and immune function compromise (Irwin et al., Am. J. Physiol 255:R744, 1988). Furthermore, clinical data suggests that CRF may be hypersecreted in the brain in depression, anxiety-related disorders, and anorexia nervosa. (DeSouza, Ann. Reports in Med. Chem. 25:215–223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., Science 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported. For example, substituted 4-thio-5-oxo-3-pyrazoline derivatives (Abreu et al., U.S. Pat. No. 5,063, 245) and substituted 2-aminothiazole derivatives (Courtemanche et al., Australian Patent No. AU-A-41399/93) have been reported as CRF receptor antagonists. These particular derivatives were found to be effective in inhibiting the binding of CRF to its receptor in the 1–10 µM range and 0.1–10 µM range, respectively.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

In brief, this invention is generally directed to CRF receptor antagonists, and more specifically to CRF receptor antagonists having the following general structure (I):

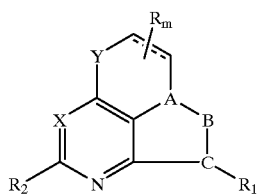

including stereoisomers, prodrugs and pharmaceutically acceptable salts thereof, wherein m, R, $R_1$, $R_2$, A, B, C, X and Y are as defined below.

The CRF receptor antagonists of this invention have utility over a wide range of therapeutic applications, and may be used to treat a variety of disorders or illnesses, including stress-related disorders. Such methods include administering an effective amount of a CRF receptor antagonist of this invention, preferably in the form of a pharmaceutical composition, to an animal in need thereof. Accordingly, in another embodiment, pharmaceutical compositions are disclosed containing one or more CRF receptor antagonists of this invention in combination with a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to compounds useful as corticotropin-releasing factor (CRF) receptor antagonists.

In a first embodiment, the CRF receptor antagonists of this invention have the following structure (I):

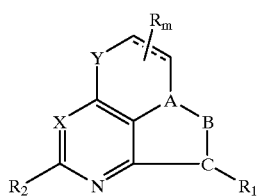

including stereoisomers, prodrugs and pharmaceutically acceptable salts thereof,
wherein:
X is nitrogen or $CR_3$;
Y is O or $S(O)_{0-2}$;
"- - -" represents an option double bond;
A and C are the same or different and independently nitrogen, carbon or CH;
B is nitrogen or $CR_4$;
with the provisos that at least one of A, B or C is nitrogen, A, B and C are not all nitrogen, and either A—B or B—C is a double bond;
R is an optional substituent which, at each occurrence, is independently alkyl, substituted alkyl, aryl, arylalkyl, alkylidenyl, heterocycle, heterocyclealkyl, alkoxy or —CO(alkoxy), wherein m is 0, 1, 2 or 3 and represents the number of R substituents;

$R_1$ is alkyl, substituted alkyl, aryl, substituted aryl, heteroaryl or substituted heteroaryl;

$R_2$ is hydrogen, alkyl, alkoxy or thioalkyl or haloalkyl;

$R_3$ is hydrogen, alkyl, halogen or haloalkyl; and

R4 is hydrogen, halogen, alkyl, alkoxy, thioalkyl or haloalkyl.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$cyclopropyl, —$CH_2$cyclobutyl, —$CH_2$cyclopentyl, —$CH_2$cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantyl, Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Alkylidenyl" represents a divalent alkyl from which two hydrogen atoms are taken from the same carbon atom, such as =$CH_2$, =$CHCH_3$, =$CHCH_2CH_3$, =$C(CH_3)CH_2CH_3$, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl (i.e., —$CH_2$phenyl), —$CH_2$—(1 or 2-naphthyl), —$(CH_2)_2$phenyl, —$(CH_2)_3$phenyl, —$CH(phenyl)_2$, and the like.

"Heteroaryl" means an aromatic heterocycle ring of 5- to 10-members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

The term "substituted" as used herein means any of the above groups (i.e., alkyl, aryl, arylalkyl, heteroaryl, heteroarylalkyl, heterocycle or heterocyclealkyl) wherein at least one hydrogen atom is replaced with a substituent. In the case of a keto substituent ("—C(=O)—") two hydrogen atoms are replaced. "Substituents" within the context of this invention include halogen, hydroxy, cyano, nitro, amino, alkylamino, dialkylamino, alkyl, alkoxy, thioalkyl, haloalkyl, hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$—NR$_a$SO$_2$R$_b$, —OR$_a$, —C(=O)R$_a$—C(=O)OR$_a$, —C(=O)NR$_a$R$_b$, —OC(=O)NR$_a$R$_b$, —SH, —SR$_a$, —SOR$_a$, —S(=O)$_2$R$_a$, —OS(=O)$_2$R$_a$, —S(=O)$_2$OR$_a$, wherein R$_a$ and R$_b$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like. Haloalkyl is a specific embodiment of substituted alkyl, wherein alkyl is substituted with one or more halogen atoms.

"Alkoxy" means an alkyl moiety attached through an oxygen bridge (i.e., —O-alkyl) such as —O-methyl, —O-ethyl, and the like.

"Thioalkyl" means an alkyl moiety attached through a sulfur bridge (i.e., —S-alkyl) such as —S-methyl, —S-ethyl, and the like.

"Alkylamino" and "dialkylamino" mean one or two alkyl moieties attached through a nitrogen bridge (i.e., —NHalkyl or —N(alkyl)(alkyl)) such as methylamino, ethylamino, dimethylamino, diethylamino, and the like.

"Hydroxyalkyl" means an alkyl substituted with at least one hydroxyl group.

Depending upon the A, B, C, X and Y substituents, representative compounds of this invention include those having the following structures (II) through (XI):

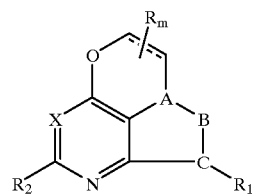

(II)

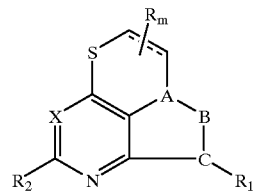

(III)

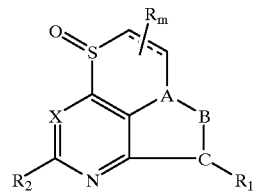

(IV)

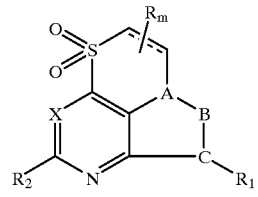

(V)

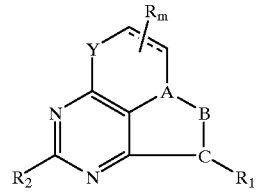

(VI)

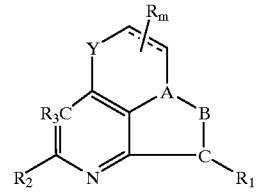

(VII)

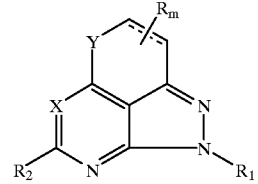

(VIII)

(IX)
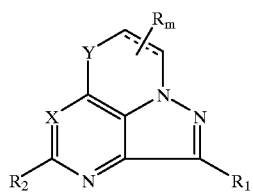

(X)
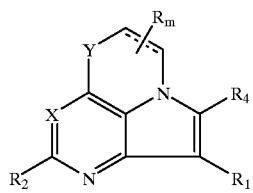

(XI)
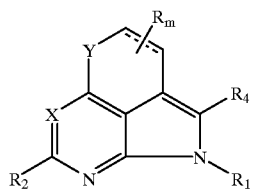

As used in the context of this invention,

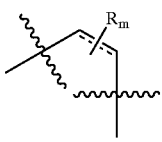

represents —CH$_2$CH$_2$— or —CH═CH— optionally substituted with 1, 2 or 3 R substituents (i.e., m=0, 1, 2 or 3). Accordingly, representative compounds of this invention include (but are not limited to) compounds having the following structures (Ia) through (Ii), where each occurrence of R is the same or different and represents a group (other than hydrogen) as defined previously:

(Ia)
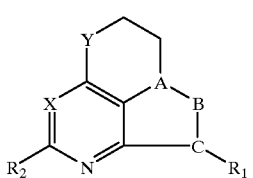

(Ib)
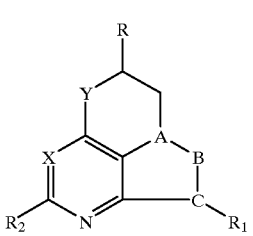

(Ic)
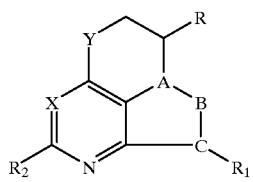

(Id)
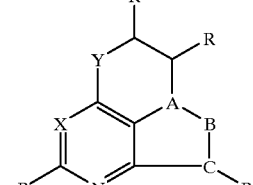

(Ie)
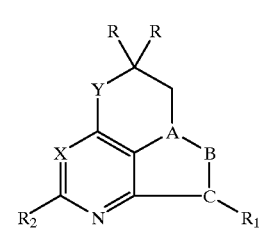

(If)
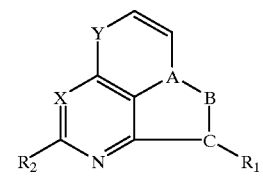

(Ig)
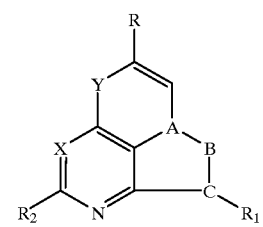

(Ih)
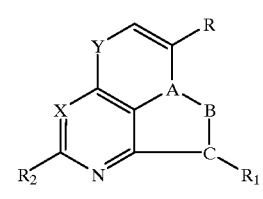

(Ii)
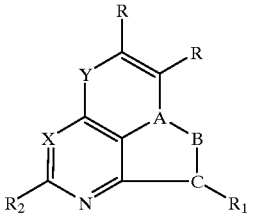

When present, representative R groups of this invention include (but are not limited) alkyl (such as methyl, ethyl, n-propyl, isopropyl and isobutyl), aryl (such as phenyl), heteroaryl (such as pyridyl), and alkylidenyl (such as ═CH$_2$ and =CHCH$_3$). In the case of R being an alkylidenyl moiety, the carbon atom to which the alkylidenyl moiety is attached must have the appropriate valency. For example, an alkylidenyl moiety would not be appropriate at the R position shown in structure (Ig) above.

In more specific embodiments of this invention, representative R$_1$ groups of this invention include (but are not limited to) 2,4-dichlorophenyl, 2,4-dimethyl-phenyl, 2-chloro-4-methylphenyl, 2-methyl-4-chlorophenyl, 2,4,6-trimethylphenyl, 2-chloro-4-methoxyphenyl, 2-methyl-4-methoxyphenyl, 2,4-dimethoxyphenyl, 2-trifluoromethyl-4-chlorophenyl, 3-methoxy-4-chlorophenyl, 2,5-dimethoxy-4-chlorophenyl, 2-methoxy-4-trichloromethylphenyl, 2-methoxy-4-isopropylphenyl, 2-methoxy-4-trifluoromethylphenyl, 2-methoxy-4-isopropylphenyl 2-methoxy-4-methylphenyl, 4-methyl-6-dimethylaminopyridin-3-yl, 4-dimethylamino-6-methyl-pyridin-3-yl, 6-dimethylamino-pyridin-3-yl and 4-dimethylamino-pyridin-3-yl.

Similarly, representative R$_2$ and R$_4$ groups include hydrogen and alkyl such as methyl and ethyl, while representative R$_3$ groups include hydrogen, halogen such as chlorine, fluorine and bromine, alkyl such as methyl and ethyl, and haloalkyl such as trifluoromethyl.

The compounds of the present invention may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

In general, the compounds of structure (I) may be made according to the organic synthesis techniques known to those skilled in this field, as well as by the representative methods set forth in the Examples. For example, the synthesis of structure (I) may generally proceed according to the following Reaction Schemes 1 through 4.

Reaction Scheme 1

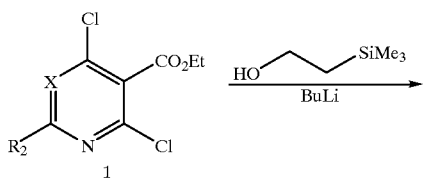

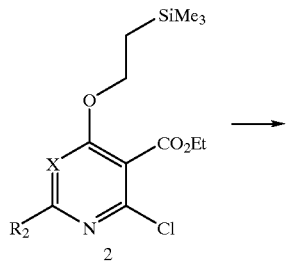

-continued

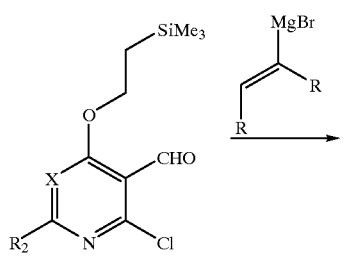

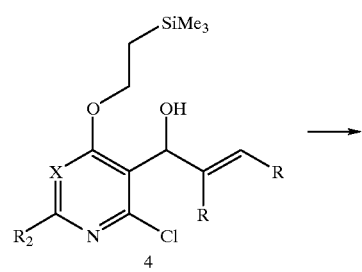

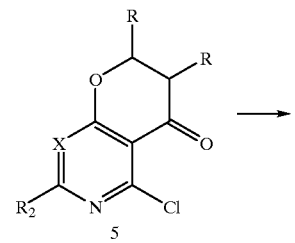

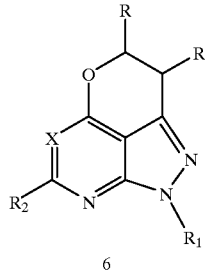

Compound 1 may be alkylated with protected diols to give the corresponding monochloroheterocycle 2. After conversion to the appropriate aldehyde 3, reaction with a Grignard reagent yields 4. Cyclization to the bicyclic ketone 5 followed by cyclization with appropriated substituted hydrazones or anilines gives 6—that is, compounds of structure (I) where Y is oxygen.

Reaction Scheme 2

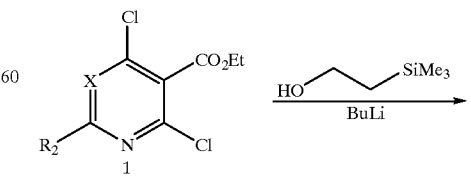

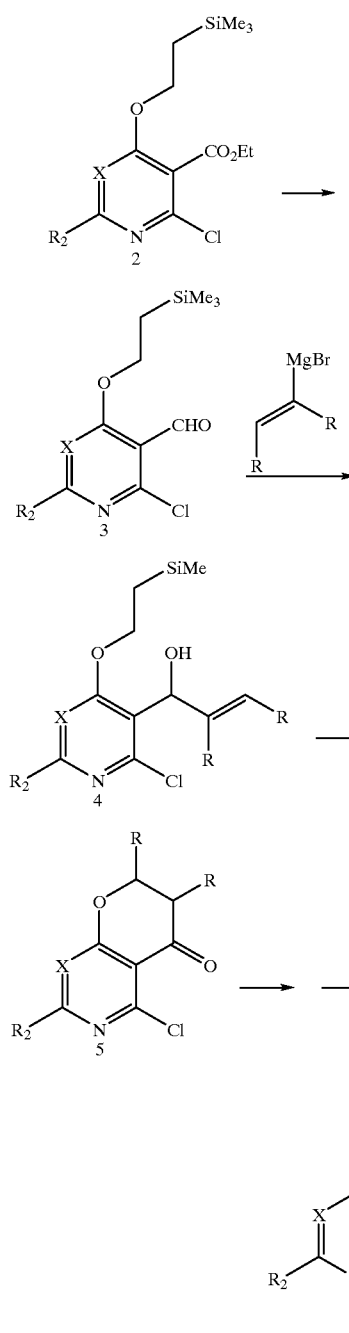

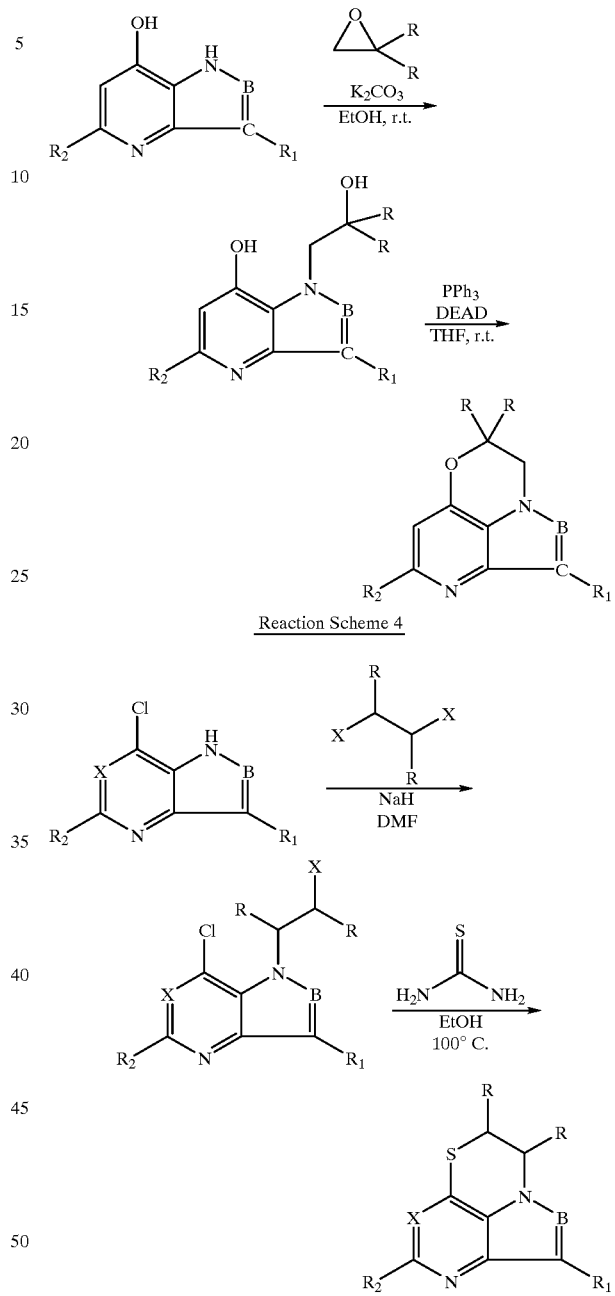

Reaction Scheme 3

Reaction Scheme 4

Compound 1 may be alkylated with protected diols to give the corresponding monochloroheterocycle 2. After conversion to the appropriate aldehyde 3, reaction with a Grignard reagent yields 4. Cyclization to the bicyclic ketone compound 5, followed by conversion of the carbonyl of compound 5 to =CHOMe, and then cyclization with appropriated substituted hydrazones or anilines gives 6—that is, compounds of structure (I) where Y is oxygen.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g., $[^{125}I]$ tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 μM. In a preferred embodiment of this invention, a CRF receptor antagonist has a $K_i$ of less than 1 μM, and more preferably less than 0.25 μM (i.e., 250 nM). As set forth in greater detail below, the $K_i$ values may be assayed by the methods set forth in Example 13.

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), pain, Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder— that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed., Mack Publishing Co., Easton, Pa. 1990.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

In another embodiment, compounds of this invention and their analogs may be used as Positron Emission Tomography (PET) ligands, Single Photon Emission Computed Tomography (SPECT) ligands, or other diagnostic radiopharmaceutical agents. Incorporation of an appropriate isotope (such as $^{11}C$ or $^{18}F$ for PET or $^{125}I$ in the case of SPECT) may provide an agent useful for the diagnosis or therapeutic management of a patient. In addition, use of a compound of the present invention may provide a physiological, functional, or biological assessment of a patient or provide disease or pathology detection and assessment.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, pain, Cushing's disease, infantile spasms, epilepsy, and substance abuse or withdrawal.

The following examples are provided for purposes of illustration, not limitation.

EXAMPLES

The CRF receptor antagonists of this invention may be prepared by the methods disclosed in Examples 1 to 12. Example 13 presents a method for determining the receptor binding activity ($K_i$), and Example 14 discloses an assay for screening compounds of this invention for CRF-stimulated adenylate cyclase activity.

Example 1
Synthesis of Representative Compounds

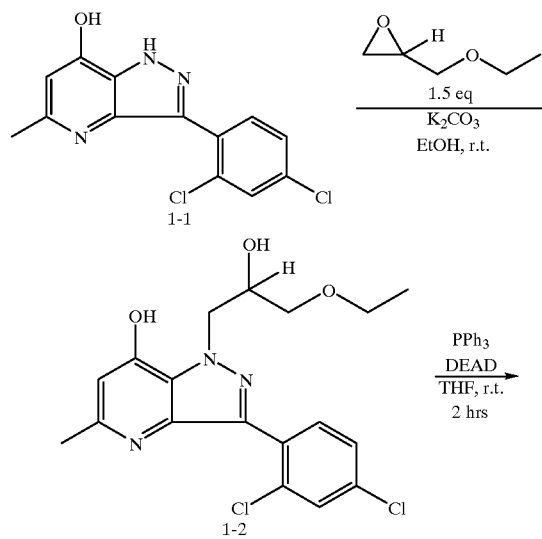

-continued

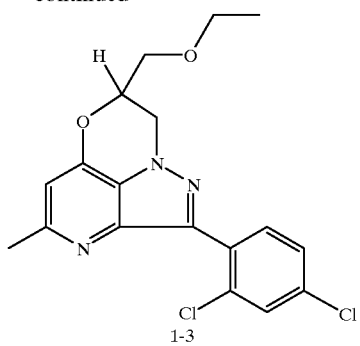

Compound 1-2

Compound 1-1 (100 mg, 0.340 mmole) and 150 mg potassium bicarbonate in 1.5 mL of ethanol were stirred at room temperature for five minutes, and one equivalent of epoxide (35 μl, 0.340 mmole) was added. After two days, the solvent was removed and the product was purified by prep-silica TLC (90:10 $CH_2Cl_2$:MeOH). The yield of intermediate 1-2 was 25 mg (20%). MS (M+1): 396.

Compound 1-3

Triphenylphosphine (1.5 eq) followed by diethyl azodicarboxylate (1.5 eq) were added to a solution of 1-2 (25 mg, 0.0631 mmole) in 1 mL of THF. After 2 hours, the reaction mixture was purified by prep-silica TLC (90:10 $CH_2Cl_2$:MeOH). 15 mg of compound 1-3 was isolated (65% yield). MS (M+1): 378. $^1H$ NMR (CDCl$_3$): δ=1.25 (3t), 2.26 (3H, s,), 3.6 (2H, q), 3.9 (2H, t), 4.4 (1H, t), 4.7 (1H,d), 4.85 (1H, m), 6.65 (1H, s), 7.4 (1H,d), 7.6(1H, s), 7.9(1H, d).

Further representative compounds were prepared by the above procedure, the structure and analytical data for which are set forth in Table 1.

TABLE 1

Analytical Data for Representative Compounds

| Cpd. No. | R | R | MW | MH+ |
|---|---|---|---|---|
| 1a | ⟩⟨⟨O⟩ | H | 377 | 378 |
| 1b | CH$_3$ | CH$_3$ | 347 | 348 |
| 1c | ⟩⟨⟨= | CH$_3$ | 359 | 360 |
| 1d | ⟩⟨⟨O⟩ | H | 363 | 364 |

TABLE 1-continued

Analytical Data for Representative Compounds

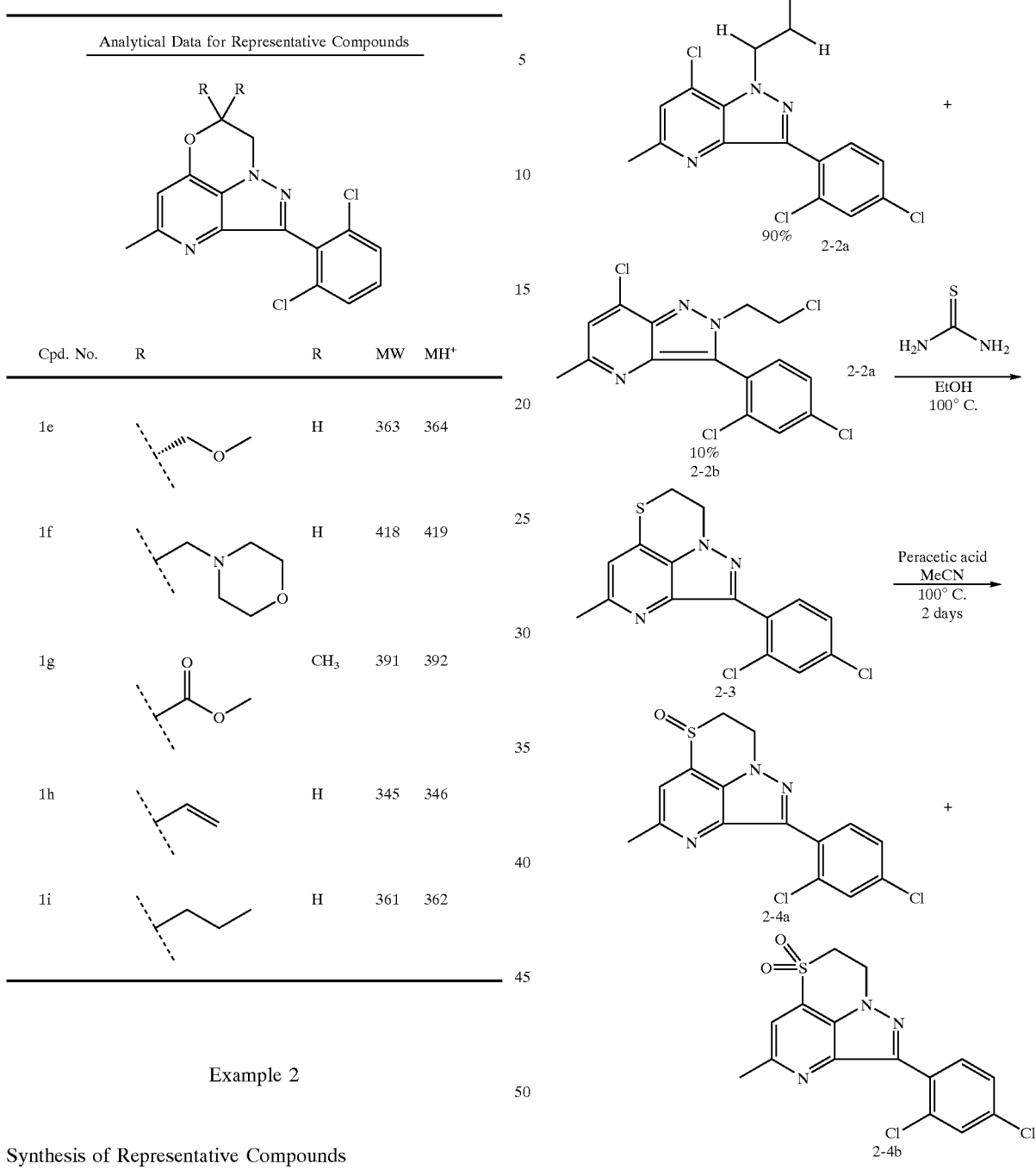

| Cpd. No. | R | R | MW | MH+ |
|---|---|---|---|---|
| 1e | -CH(CH₃)OCH₃ | H | 363 | 364 |
| 1f | -CH₂-morpholine | H | 418 | 419 |
| 1g | -C(O)OCH₃ | CH₃ | 391 | 392 |
| 1h | -CH₂CH=CH₂ | H | 345 | 346 |
| 1i | -CH₂CH₂CH₃ | H | 361 | 362 |

Example 2

Synthesis of Representative Compounds

Compound 2-2

Compound 2-1 (45 mg, 0.143 mmole), NaH (10 mg) and 1,2-dichloroethane (80 μl) in 2 mL of DMF were stirred at room temperature for 16 hrs. Reaction gave two isomeric products in 9:1 ratio, with 2-2a being the major product. After removal of DMF, the product was redissolved in ethyl acetate and washed with brine three times. The organic layers were combined, dried over sodium sulfate and evaporated to give 50 mg of compound 2-2a (92% yield). MS (M+1): 376

Compound 2-3

Compound 2-2a (50 mg, 0.13 mmole) and excess of thiourea (100 mg) in 0.5 mL of ethanol were heated to 80° C. for 16 hours. The reaction mixture was filtered and purified by reverse phase prep HPLC yielding compound 2-3 (26 mg, 65% yield). MS (M+1): 336. $^1$H NMR (CDCl$_3$) δ=2.85 (3H, s), 3.7 (2H, bs), 4.8 (2H, bs), 7.29 (1H, s) 7.4 (1H, d), 7.48 (1H, d), 7.56 (1H, s).

Compound 2-4

Compound 2-2a (50 mg, 0.133 mmole) in 0.5 mL of MeCN and 3 mL of peracetic acid (32% wt.) were stirred over 16 hrs at room temperature. Product 2-4a and 2-4b were isolated by reverse phase prep HPLC. 2-4a MS (M+1): 353, 2-4b MS (M+1): 367. 2-4a $^1$H NMR (CDCl$_3$) δ: 2.85 (3H, s), 3.8 (2H, t), 5.1 (2H, t), 7.42 (1H, dd), 7.59 (1H,s), 7.61(1H, d), 7.80 (1H, d).

Further representative compounds were prepared by the above procedure, the structure and analytical data for which are set forth in Table 2.

TABLE 2

Analytical Data for Representative Compounds

| Cpd. No. | R | R | MW | LCMS |
|---|---|---|---|---|
| 2a | H | H | 336.25 | 336 |
| 2b | ⌁⌁⌁/\ | H | 364.30 | 364 |
| 2c | ⌁⌁⌁/\O/ | H | 380.30 | 380.0 |
| 2d | ⌁⌁⌁/\ | ⌁⌁⌁/\ | 392.35 | 392 |
| 2e | H | ⌁⌁⌁/C(O)OEt | 408.31 | 408 |

2b $^1$H NMR(CDCl$_3$) δ = 1.25(3H, t), 2.0(2H, m), 2.80(3H, s), 3.9(1H, t), 4.4(1H, t), 4.9(1H, t), 7.21(1H, s), 7.38(1H, dd), 7.52(1H, s), 7.56(1H, d).
2c $^1$H NMR(CDCl$_3$) δ = 1.2(3H,t), 2.80(3H, s), 3.56(1H, dd), 3.7(1H, dd), 3.8(1H, t), 3.9(2H, m), 6.05(1H, s), 7.26(1H, s), 7.40(1H, dd), 7.55(1H, dd).
2d $^1$H NMR(CDCl$_3$) δ = 1(3H, t), 1.25(3H, t), 2(4H, 2 fused m), 2.85(3H, s), 3.9(1H, m), 4.8(1H, m), 7.21(1H, s), 7.38(1H, dd), 7.52(1H, d), 7.56 (1H, d).
2e $^1$H NMR(CDCl$_3$) δ = 1.35(3H, t), 2.85(3H, s), 4.3(2H, q), 4.6(1H, t), 5(2H, m) 7.26(1H, s), 7.40(1H, dd), 7.52(1H, s), 7.57(1H, d).

Example 3

Synthesis of Representative Compounds

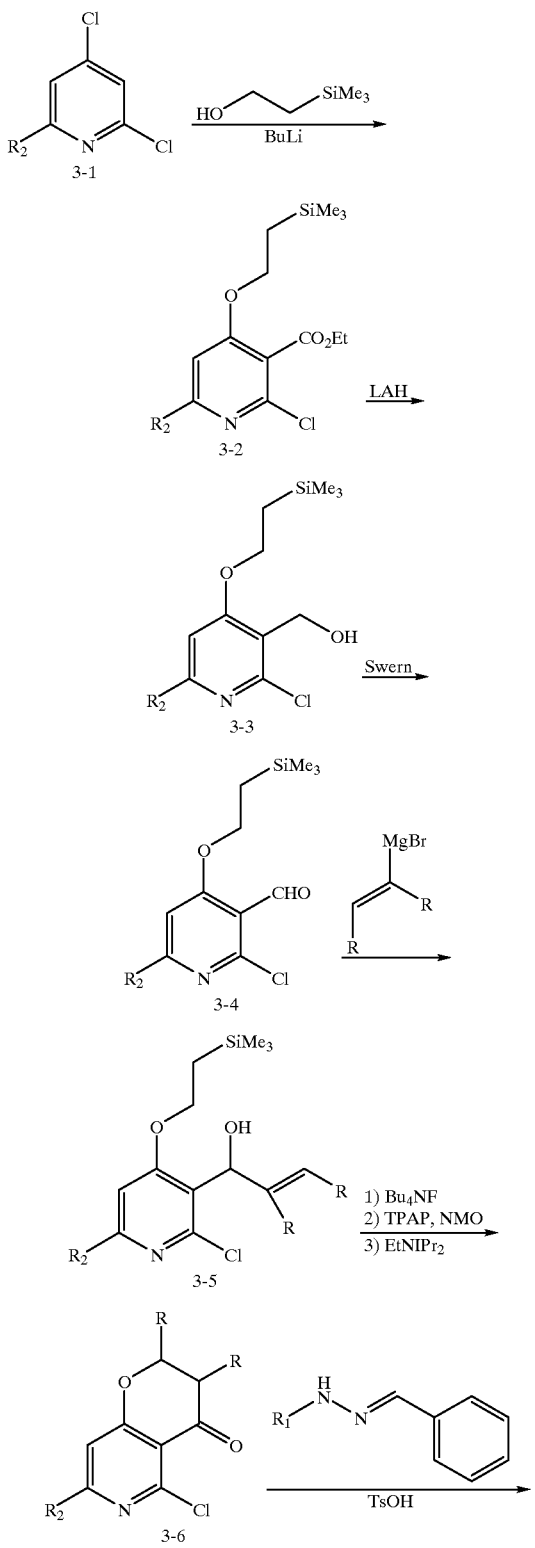

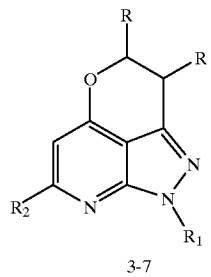

3-7

Compound 3-2

Trimethylsilylethanol is treated with n-butyllithium at −78° C. in THF. After 15 minutes dichloropyridine 3-1 is added and the mixture is allowed to warm to room temperature. The mixture is then heated at 50 ° C. for 2 hours. Upon cooling to room temperature the mixture is poured into saturated NH$_4$Cl and extracted with ethyl acetate. The organic layers are combined and washed three times with water and brine. The organic phase is dried (MgSO$_4$) and concentrated in vacuo. Purification via flash chromatography gives the desired product 3-2.

Compound 3-3

Chloropyridine 3-2 is dissolved in THF and added to a stirred suspension of LAH in THF at −78 ° C. The mixture is stirred for 6 h at this temperature and 1 h at −30° C. The mixture is then treated cautiously with water, 15% aqueous NaOH and water with vigorous stirring. The mixture is warmed to room temperature and filtered. The white precipitate is washed liberally with ethyl acetate. The combined organic portions are dried (MgSO$_4$) and concentrated under vacuum. Purification via flash chromatography gives the desired product 3-3.

Compound 3-4

DMSO (6 equivalents) is added to a stirred solution of oxalyl chloride (3 equivalents) in dichloromethane at −70° C. After 15 min, alcohol 3-3 (1 equivalent) in dichloromethane is added, followed by triethylamine. The mixture is allowed to warm to room temperature and stirred for 1 h. The mixture is washed with aqueous sodium bicarbonate (75 mL), dried (MgSO$_4$), and concentrated under vacuum. Purification via flash chromatography gives the desired product 3-4.

Compound 3-5

Alkenylmagnesium bromide in THF (1 equivalent) is added to a stirred solution of aldehyde 3-4 (1equivalent) in THF at −78° C. The mixture is stirred at this temperature for 30 min, warmed to room temperature and quenched with aqueous sodium bicarbonate The mixture is then extracted with ethyl acetate and the combined extracts are dried (MgSO$_4$) and concentrated under vacuum. Purification via flash chromatography gives the desired product 3-5.

Compound 3-6

The allylic alcohol 3-5 is treated with tetrabutylammonium fluoride in THF. After 1 hour the mixture is diluted with ethyl acetate and washed with saturated ammonium chloride, dried (MgSO$_4$) and concentrated in vacuo. The crude mixture and N-methylmorpholine N-oxide (1.5 equivalents) are dissolved in dichloromethane and stirred in the presence of 4 angstrom molecular sieves for 20 min. Catalytic tetrapropylammonium perruthenate is added and the mixture was stirred for 1 hour. The mixture is filtered (Celite) and concentrated under vacuum. The crude mixture is dissolved in 5 equivalents of diisopropylethylamine and heated at 50° C. for 6 hours. The resultant mixture is concentrated in vacuo and purification via flash chromatography provides the desired product 3-6.

Compound 3-7

Compound 3-6 (one equivalent), TsOH.H$_2$O (one equivalent) and hydrazone (one equivalent) are heated at 140° C. for 5 hours. The heating is halted and the mixture is allowed to return to room temperature. The mixture is diluted with NaHCO$_3$ and extracted with EtOAc. The combined extracts are dried (MgSO$_4$) and concentrated in vacuo. The residue is purified by flash chromatography to give the final product 3-7.

Example 4

Synthesis of Representative Compounds

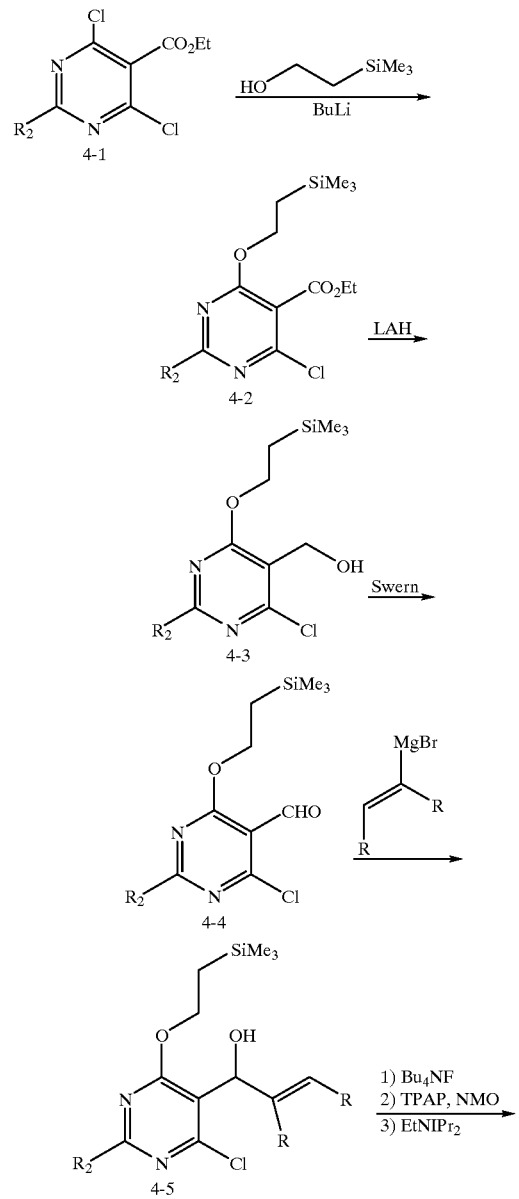

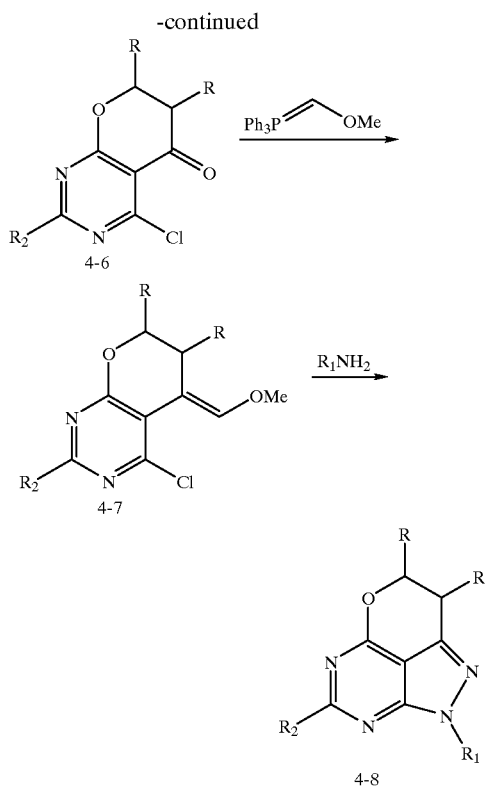

Compound 4-2

Trimethylsilylethanol is treated with n-butyllithium at −78° C. in THF. After 15 minutes dichloropyrimidine 4-1 is added and the mixture is allowed to warm to room temperature. The mixture is then heated at 50° C. for 2 hours. Upon cooling to room temperature the mixture is poured into saturated NH$_4$Cl and extracted with ethyl acetate. The organic layers are combined and washed three times with water and brine. The organic phase is dried (MgSO$_4$) and concentrated in vacuo. Purification via flash chromatography gives the desired product 4-2.

Compound 4-3

The chloropyrimidine 4-2 is dissolved in THF and added to a stirred suspension of LAH in THF at −78° C. The mixture is stirred for 6 h at this temperature and 1 h at −30° C. The mixture is then treated cautiously with water, 15% aqueous NaOH and water with vigorous stirring. The mixture is warmed to room temperature and filtered. The white precipitate is washed liberally with ethyl acetate. The combined organic portions are dried (MgSO$_4$) and concentrated under vacuum. Purification via flash chromatography gives the desired product 4-3.

Compound 4-4

DMSO (6 equivalents) is added to a stirred solution of oxalyl chloride (3 equivalents) in dichloromethane at −70° C. After 15 min, alcohol 4-3 (1 equivalent) in dichloromethane is added, followed by triethylamine. The mixture is allowed to warm to room temperature and stirred for 1 h. The mixture is washed with aqueous sodium bicarbonate (75 mL), dried (MgSO$_4$), and concentrated under vacuum. Purification via flash chromatography gives the desired product 4-4.

Compound 4-5

Alkenylmagnesium bromide in THF (1 equivalent) is added to a stirred solution of aldehyde 4-4 (1 equivalent) in THF at −78° C. The mixture is stirred at this temperature for 30 min, warmed to room temperature and quenched with aqueous sodium bicarbonate The mixture is extracted with ethyl acetate and the combined extracts are dried (MgSO$_4$) and concentrated under vacuum. Purification via flash chromatography gives the desired product 4-5.

Compound 4-6

The allylic alcohol 4-5 is treated with tetrabutylammonium fluoride in THF. After 1 hour the mixture is diluted with ethyl acetate and washed with saturated ammonium chloride, dried (MgSO$_4$) and concentrated in vacuo. The crude mixture and N-methylmorpholine N-oxide (1.5 equivalents) are dissolved in dichloromethane and stirred in the presence of 4 angstrom molecular sieves for 20 min. Catalytic tetrapropylammonium perruthenate is added and the mixture stirred for 1 hour. The mixture is filtered (Celite) and concentrated under vacuum. The crude mixture is dissolved in 5 equivalents of diisopropylethylamine and heated at 50° C. for 6 hours. The resultant mixture is concentrated in vacuo and purification via flash chromatography provides the desired product 4-6.

Compound 4-7

Lithium diisopropylamide in THF is added to a solution of the 1 equivalent of phosphine oxide in THF at −25° C. After 15 min, one equivalent of compound 4-6 in THF is added and the mixture stirred for 15 minutes. Sodium hydride is then added, the mixture is warmed to room temperature and stirred for 16 hrs. The mixture is diluted with water (15 ml) and extracted with EtOAc (4×10 ml) . The combined extracts are dried (MgSO$_4$), concentrated in vacuo and the residue is purified by flash chromatography to give the desired product 4-7.

Compound 4-8

Compound 4-7 (one equivalent), TsOH.H$_2$O (two equivalents) and the aniline (5 equivalents) are heated at 130° C. for 16 hrs. The mixture is cooled to room temperature, diluted with aqueous NaHCO$_3$ (2 ml) and extracted with EtOAc (4×2 ml). The combined extracts are dried (MgSO$_4$), concentrated in vacuo and the residue is purified by flash chromatography to give the desired product 4-8.

Example 5

Synthesis of Representative Compounds

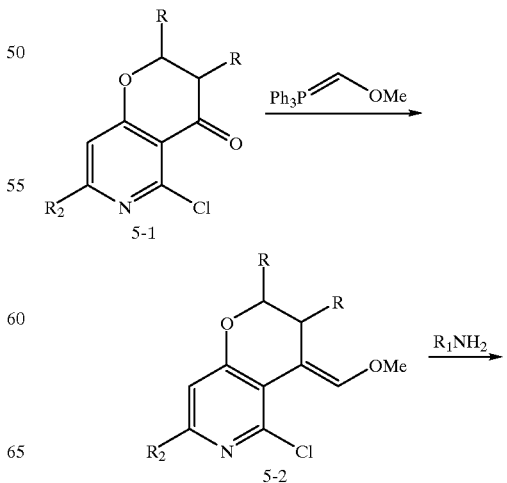

-continued

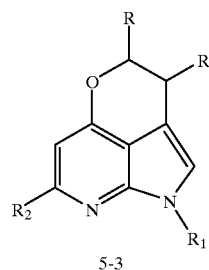

5-3

Compound 5-2

Lithium diisopropylamide in THF is added to a solution of the 1 equivalent of phosphine oxide in THF at −25° C. After 15 min, one equivalent of compound 5-1 in THF is added and the mixture is stirred for 15 minutes. Sodium hydride is then added, the mixture is warmed to room temperature and stirred for 16 hrs. The mixture is diluted with water (15 ml) and extracted with EtOAc (4×10 ml). The combined extracts are dried (MgSO$_4$), concentrated in vacuo and the residue is purified by flash chromatography to give 5-2.

Compound 5-3

Compound 5-2 (one equivalent), TsOH.H$_2$O (two equivalents) and the aniline (5 equivalents) is heated at 130° C. for 16 hrs. The mixture is cooled to room temperature, diluted with aqueous NaHCO$_3$ (2 ml) and extracted with EtOAc (4×2 ml). The combined extracts are dried (MgSO$_4$), concentrated in vacuo and the residue is purified by flash chromatography to give product 5-3.

Example 6
Synthesis of Representative Compounds

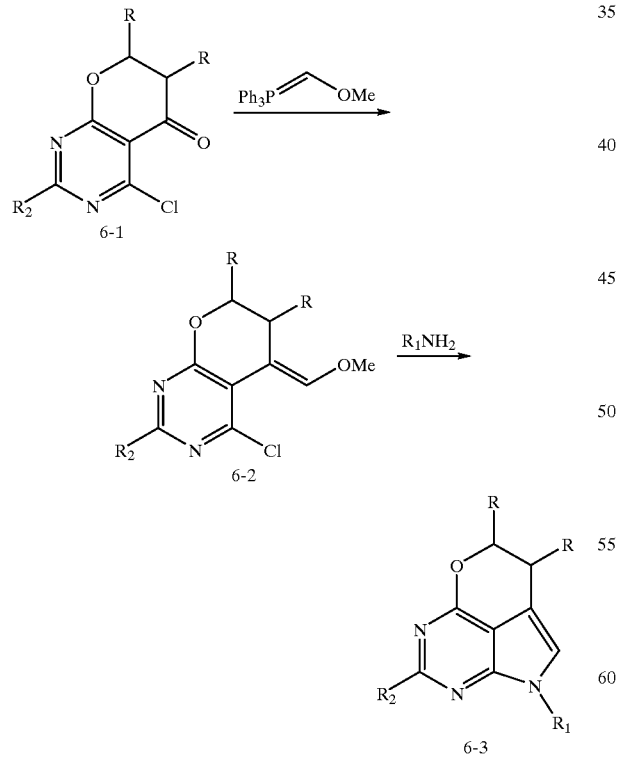

Compound 6-2

Lithium diisopropylamide in THF is added to a solution of the 1 equivalent of phosphine oxide in THF at −25° C. After 15 min, one equivalent of compound 6-1 in THF is added and the mixture is stirred for 15 minutes. Sodium hydride is then added, the mixture is warmed to room temperature and stirred for 16 hours. The mixture is diluted with water and extracted with EtOAc. The combined extracts are dried (MgSO$_4$), concentrated in vacuo and the residue is purified by flash chromatography to give 6-2.

Compound 6-3

Compound 6-2 (one equivalent), TsOH.H$_2$O (two equivalents) and the aniline (5 equivalents) is heated at 130° C. for 16 hrs. The mixture is cooled to room temperature, diluted with aqueous NaHCO$_3$ ) and extracted with EtOAc. The combined extracts are dried (MgSO$_4$), concentrated in vacuo and the residue is purified by flash chromatography yielding 6-3.

Example 7
Synthesis of Representative Compounds

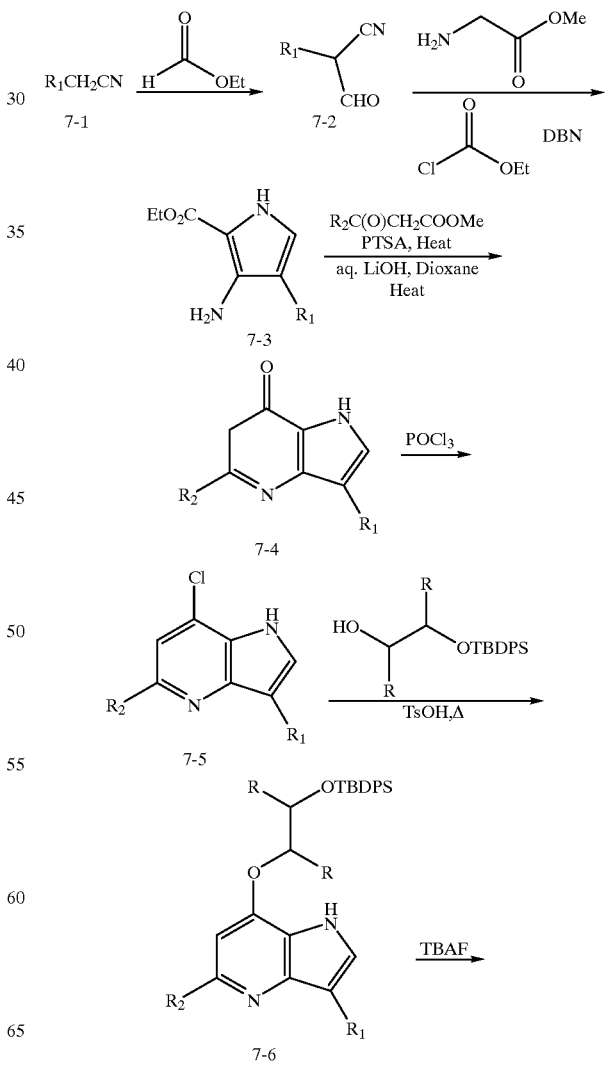

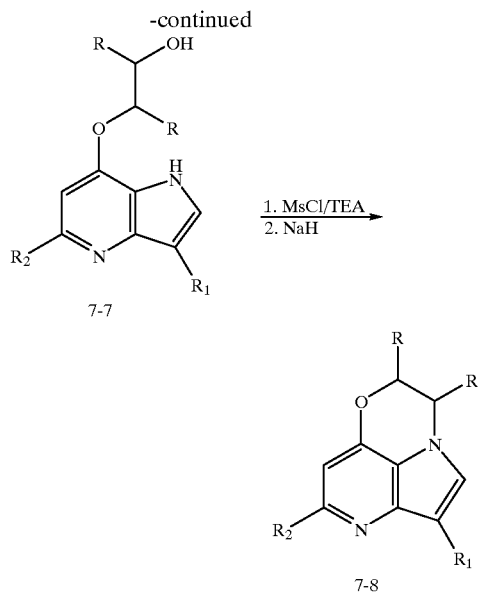

Compound 7-2

Under nitrogen atmosphere, ethyl formate (7.38 g, 99.6 mmol) in anhydrous THF (100 mL) is added dropwise to a stirred mixture of NaH (1.75 g, 72.9 mmol) and Compound 7-1 (37.5 mmol) in THF (100 mL). The mixture is stirred overnight. Additional portions of NaH and HCO$_2$Et (2 equiv each) are added, and the mixture is refluxed for 30 min and then stirred at room temperature overnight. After solvent evaporation, the residue in ice cold water (100 mL) is adjusted to pH 6 with cold 6 N HCl and is extracted with CHCl$_3$ (3×100 mL). The extract is washed with water (100 mL), dried (Na$_2$SO$_4$), and evaporated. The residue is triturated with hexane, which is decanted. Column chromatography of the residue on silica gel (using CHCl$_3$ as eluant) gives compound 7-2.

Compound 7-3

A solution of compound 7-2 (5.31 mmol), methyl glycinate hydrochloride (1.00 g, 7.97 mmol), and sodium acetate (0.654 g, 7.97 mmol) in MeOH (40 mL) and H$_2$O (10 mL) is stirred at room temperature for 48 hr. The mixture is extracted with CHCl$_3$ (2×25 mL), and the organic extract is washed with water (20 mL), dried (Na$_2$SO$_4$), and evaporated. The residue (4.5 mmol) in dry CH$_2$Cl$_2$ (25 mL) is cooled to 0° C. and treated with 1,5-diazabicyclo(4.3.0)non-5-ene (DBN, 1.12 g, 9.04 mmol) followed by ethyl chloroformate (0.735 g, 6.78 mmol). After refrigeration for 24 h, 0.2 mL of DBN and 0.1 mL of ClCO$_2$Et are added to consume the small quantity of remaining starting material. An additional equivalent of DBN (0.6 g) is added, and the mixture is refrigerated for 20 hrs. Solvent is evaporated and the gummy residue is chromatographed on a silica gel column (CHCl$_3$ eluant) to give compound 7-3.

Compound 7-4

A solution of compound 7-3 (9.9 mmol), ethyl acetoacetate (9.9 mmol) and p-toluenesulfonic acid monohydrate (0.01 mmol) in 10 mL of xylene is refluxed for 2 hrs. Half of solvent is removed by slow distillation over 1 hour. The solution is allowed to cool to room temperature and a solution of potassium t-butoxide (9.8 mmol) in 24 mL of ethanol is added. This mixture is heated to 80° C. for 2 hrs. The mixture is diluted with ethyl acetate and washed with saturated NaCl solution. The organic layer is dried with sodium sulfate and concentrated in vacuo. The residue is triturated with ether. The solid obtained is treated with an aqueous solution of LiOH (18 mL, 1M) in methanol and the mixture is heated at reflux for 18 hrs. The solution is poured into a solution of 1M HCl (18 mL). The solution is extracted with ethyl acetate, washed with brine, dried with sodium sulfate and concentrated in vacuo to give a solid which is heated in diphenyl ether at 230° C. for 1.5 hrs. The solid 7-4 obtained after diluting with ether is dried in vacuo.

Compound 7-

The solid 7-4 is heated at 100° C. in POCl$_3$ for 2 hrs then is allowed to cool to room temperature. The reaction mixture is poured into ice and neutralized with NaHCO$_3$. The solution is extracted with ethyl acetate. The organic layer is washed with brine, dried with sodium sulfate and concentrated in vacuo. Compound 7-5 is purified by flash chromatography on silica gel silica gel eluting with ethyl acetate-hexane (1:3).

Compound 7-6

Compound 7-5 is condensed with one equivalent of the t-butyldiphenylsilyl protected diol in the presence of sodium hydride in dry DMF. The mixture is then heated at 50° C. for 6 hours. Upon cooling to room temperature the mixture is poured into saturated NH4Cl and extracted with ethyl acetate. The organic layers are combined and washed three times with water and brine. The organic phase is dried (MgSO$_4$) and concentrated in vacuo. Purification via flash chromatography gives the desired product 7-6.

Compound 7-7

Compound 7-6 is treated with 1M Bu$_4$NF in THF. After 3 hours the mixture is washed with water and extracted with EtOAc. The organic phase is dried (MgSO$_4$) and concentrated in vacuo. Purification via flash chromatography gives the desired desilylated product 7-7.

Compound 7-8

Compound 7-7 is treated with methanesulfonyl chloride and triethylamine in CH$_2$Cl$_2$ at 0° C. After three hours the mixture is washed with saturated NH$_4$Cl and brine. The organic phase is dried (MgSO$_4$) and concentrated in vacuo. Without further purification the mesylate is treated with NaH in THF at 0° C. After one hour the reaction mixture is poured into saturated NH$_4$Cl and extracted with EtOAc. The organic phase is dried (MgSO$_4$) and concentrated in vacuo. Purification via flash chromatography gives the desired product 7-8.

Example 8

Synthesis of Representative Compounds

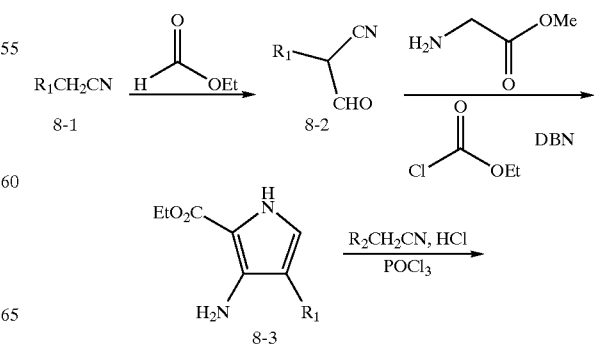

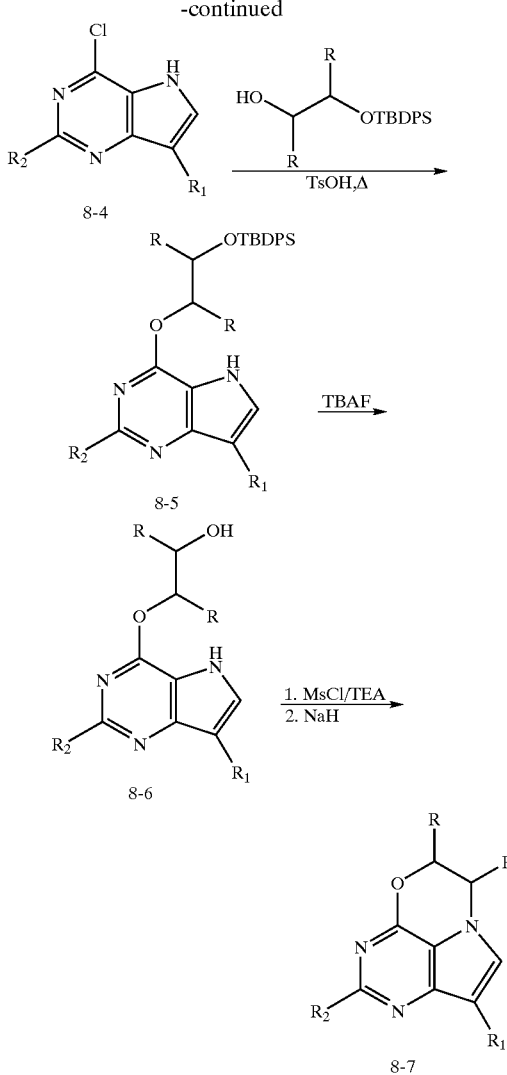

Compound 8-2

Under nitrogen atmosphere, ethyl formate (7.38 g, 99.6 mmol) in anhydrous THF (100 mL) is added dropwise to a stirred mixture of NaH (1.75 g, 72.9 mmol) and Compound 8-1 (37.5 mmol) in THF (100 mL). The mixture is stirred over night. Additional portions of NaH and $HCO_2Et$ (2 equiv each) are added, and the mixture is refluxed for 30 min and then stirred at room temperature overnight. After solvent evaporation, the residue in ice cold water (100 mL) is adjusted to pH 6 with cold 6 N HCl and is extracted with $CHCl_3$ (3×100 mL). The extract is washed with water (100 mL), dried ($Na_2SO_4$), and evaporated. The residue is triturated with hexane, which is decanted. Column chromatography of the residue on silica gel (using $CHCl_3$ as eluant) gives compound 8-2.

Compound 8-3

A solution of compound 8-2 (5.31 mmol), methyl glycinate hydrochloride (1.00 g, 7.97 mmol), and sodium acetate (0.654 g, 7.97 mmol) in MeOH (40 mL) and $H_2O$ (10 mL) is stirred at room temperature for 48 hrs. The mixture is extracted with $CHCl_3$ (2×25 mL), and the organic extract is washed with water (20 mL), dried ($Na_2SO_4$), and evaporated. The residue (4.5 mmol) in dry $CH_2Cl_2$ (25 mL) is cooled to 0° C. and treated with 1,5-diazabicyclo(4.3.0)non-5-ene (DBN, 1.12 g, 9.04 mmol) followed by ethyl chloroformate (0.735 g, 6.78 mmol). After refrigeration for 24 h, 0.2 mL of DBN and 0.1 mL of $ClCO_2Et$ are added to consume the small quantity of remaining starting material. An additional equivalent of DBN (0.6 g) is added, and the mixture is refrigerated for 20 hrs. Solvent is evaporated and the gummy residue is chromatographed on a silica gel column ($CHCl_3$ eluant) to give compound 8-3.

Compound 8-4

HCl gas is bubbled into a solution of compound 8-3 and acetonitrile in dioxane at room temperature. The reaction is monitored by TLC until all starting material is consumed. 10% aqueous ammonium hydroxide is added until the mixture is basic, followed by extraction with ethyl acetate. The organic layer is washed with water, dried over $MgSO_4$ and then evaporated to give a brown solid. The solid is dissolved in $POCl_3$ and is heated at 100° C. for 2 hrs. The excess $POCl_3$ is evaporated in vacuo and the residue is neutralized with 2N NaOH. Extraction with ethyl acetate followed by drying over $MgSO_4$ and evaporation gives a residue which is purified by flash chromatography on silica gel (Hexane/EtOAc, 4:1) to give compound 8-4.

Compound 8-5

Compound 8-4 is condensed with one equivalent of the t-butyldiphenylsilyl protected diol in the presence of sodium hydride in dry DMF. The mixture is then heated at 50° C. for 6 hrs. Upon cooling to room temperature the mixture is poured into saturated $NH_4Cl$ and extracted with ethyl acetate. The organic layers are combined and washed three times with water and brine. The organic phase is dried ($MgSO_4$) and concentrated in vacuo. Purification via flash chromatography gives the desired product 8-5.

Compound 8-6

Compound 8-5 is treated with 1M $Bu_4NF$ in THF. After 3 hours the mixture is washed with water and extracted with EtOAc. The organic phase is dried ($MgSO_4$) and concentrated in vacuo. Purification via flash chromatography gives the desired desilylated product 8-6.

Compound 8-7

Compound 8-6 is treated with methanesulfonyl chloride and triethylamine in $CH_2Cl_2$ at 0° C. After three hours the mixture is washed with saturated $NH_4Cl$ and brine. The organic phase is dried ($MgSO_4$) and concentrated in vacuo. Without further purification the mesylate is treated with NaH in THF at 0° C. After one hour the reaction mixture is poured into saturated $NH_4Cl$ and extracted with EtOAc. The organic phase is dried ($MgSO_4$) and concentrated in vacuo. Purification via flash chromatography gives the desired product 8-7.

Example 9

Synthesis of Representative Compounds

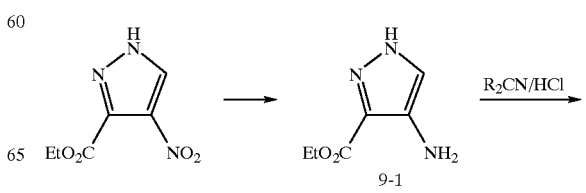

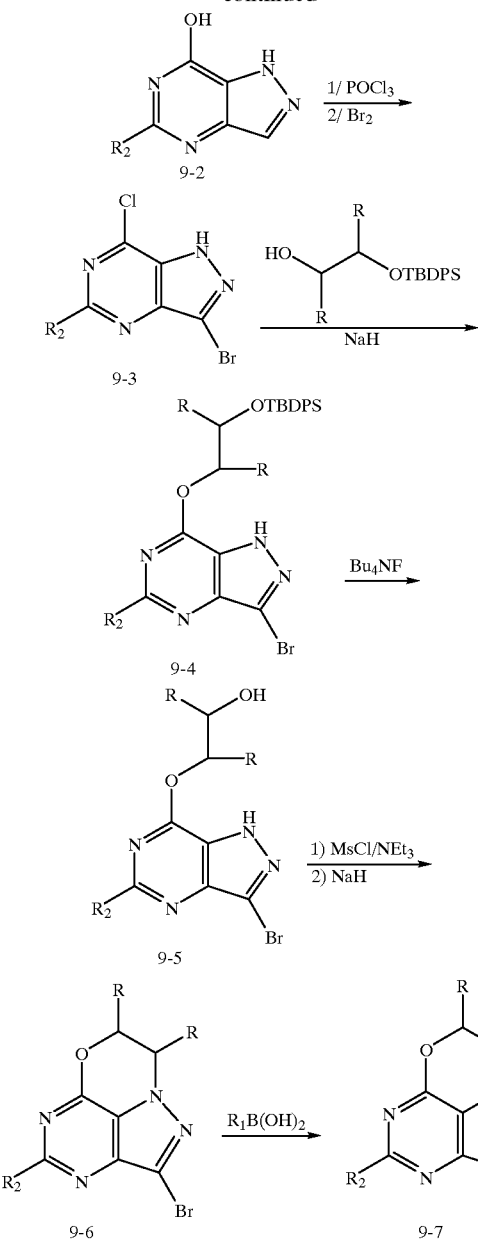

Compound 9-1

The 4-nitro pyrazole is added to a suspension of palladium on carbon 10% in ethanol (100 mL). The mixture is shaken for 3 hours under hydrogen gas (40 psi) at room temperature. The end of reaction checked by TLC (ethylacetate/hexane 1/1, nitropyrazole Rf 0.6, UV active, amino-pyrazole Rf 0.1, UV active). The catalyst is removed by filtration through celite and the solvents are evaporated. The product 9-1, a burgundy solid, is used in the following step without purification. The reaction is quantitative.

Compound 9-2

A solution of 4-amino pyrazole 2 (0.4 mol, 1 eq) is stirred in a mixture of acetonitrile/dioxane. HCl gas is bubbled through. When all the starting material is reacted, the reaction mixture is basified with $NH_4OH$ and extracted with ethyl acetate. The organic layers are combined and are washed three times with water and brine. The organic phase is dried ($MgSO_4$) and concentrated in vacuo. Purification via flash chromatography gives the desired product 9-2.

Compound 9-3

Compound 9-2 is heated at 90° C. in a mixture of $POCl_3$/acetonitrile (90 mL/100 mL) for 5 hours. After cooling down to room temperature, the reaction mixture is poured onto ice and is neutralized with a 6N NaOH solution. The product is purified by liquid chromatography. The chloro compound is dissolved in 800 mL of a mixture of water/methanol (1/1) cooled in an ice-bath. A bromine solution (12 mL of bromine in 100 mL H2O/MeOH 1/1) is added dropwise to the cooled mixture. After 10 minutes, the solution is clearer and the LC/MS shows no chloro compound. The reaction mixture is concentrated, extracted with ethyl acetate (3×10 mL). The organic phases are combined, washed with water (2×50 mL), a brine solution (1×50 mL) and dried with sodium thiosulfate. The product is purified by liquid chromatography (ethyl acetate/hexane 1/1 Rf 0.7) to give 9-3.

Compound 9-4

Compound 9-3 is condensed with one equivalent of the t-butyldiphenylsilyl protected diol in the presence of sodium hydride in dry DMF. The mixture is then heated at 50° C. for 6 hours. Upon cooling to room temperature the mixture is poured into saturated $NH_4Cl$ and is extracted with ethyl acetate. The organic layers are combined and washed three times with water and brine. The organic phase is dried ($MgSO_4$) and concentrated in vacuo. Purification via flash chromatography gives the desired product 9-4.

Compound 9-6

The silyl protected alcohol 9-4 is treated with 1M $Bu_4NF$ in THF. After 3 hours the mixture is washed with water and extracted with EtOAc. The organic phase is dried ($MgSO_4$) and concentrated in vacuo. Purification via flash chromatography gives the desired desilylated product. The desilylated product 9-5 is then treated with methanesulfonyl chloride and triethylamine in $CH_2Cl_2$ at 0° C. After three hours the mixture is washed with saturated $NH_4Cl$ and brine. The organic phase is dried ($MgSO_4$) and concentrated in vacuo. Without further purification the mesylate is treated with NaH in THF at 0° C. After one hour the reaction mixture is poured into saturated $NH_4Cl$ and is extracted with EtOAc. The organic phase is dried ($MgSO_4$) and concentrated in vacuo. Purification via flash chromatography gives the desired product 9-6.

Compound 9-7

The compound 9-6 is reacted with with 1.1 eq of a boronic acid, 3 eq of sodium carbonate and 0.1 eq of tetrakis (triphenylphosphine) in toluene. The mixture is heated at reflux overnight. It is then cooled, diluted with ethyl acetate, and washed with saturated ammonium chloride solution. The organic layers are combined and washed three times with water and brine. The organic phase is dried ($MgSO_4$) and concentrated in vacuo. Purification via flash chromatography gives the desired product 9-7.

Example 10
Synthesis of Representative Compounds

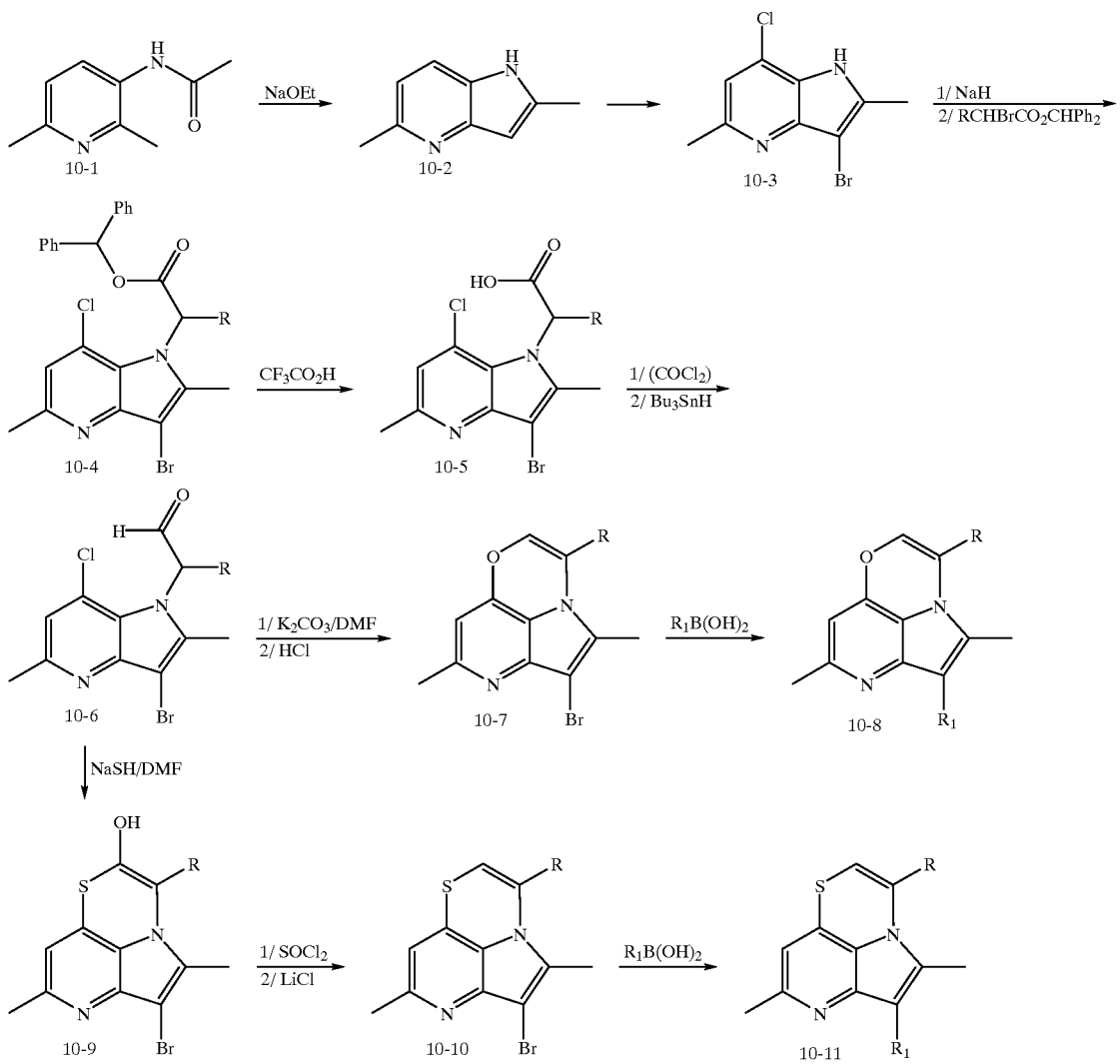

Compound 10-1

2,6-Dimethyl 3-amino pyridine (1 eq, *J. Chem. Soc.*, 2952-57, 1950) is dissolved in pyridine and 1.5 eq of acetic anhydride is added. The mixture is stirred at room temperature for 1 day. Solvents are evaporated, water is added and the product is extracted with ethyl acetate. The organic layers are combined, washed with water and brine, dried with $MgSO_4$ and concentrated. The residue is purified by liquid chromatography to give 10-1.

Compound 10-2

A solution of sodium (1.7 g) and compound 10-1 (5 g) in anhydrous ethanol is evaporated to dryness and the residue is heated under dry hydrogen at 200° C. The temperature is slowly raised to 320° C. and maintained there for 15 minutes during which time the mixture darkens and a vigorous evolution of gas occurs. To the cooled mixture, water (100 mL) is added and the insoluble pale yellow residue filtered off, dried and sublimed at 150° C./0.5 mm to give 10-2.

Compound 10-3

To compound 10-2 in acetic acid, bromine (2.2 g) in acetic acid is added dropwise and the mixture set aside. The needles which separated are crystallized from glacial acetic acid and are dissolved in water. The addition of 1 equivalent of N-sodium hydroxide gives compound 10-3.

Compound 10-4

A suspension of chloro bromo pyrrolopyridine 10-3 (1 eq) in DMF is added to a NaH dispersion (1.2 eq) in DMF at room temperature. The mixture is stirred for 30 minutes. The benzhydryl bromoacetate (2 eq) is added and the reaction mixture is stirred for four hours. The reaction mixture is then poured into water and is extracted with dichloromethane. The organic layers are combined, washed with water and brine, dried with $MgSO_4$ and concentrated. The residue is purified by liquid chromatography ot give compound 10-4. (*J. Heterocyclic Chemistry* 1991, 1067).

Compound 10-5

To a solution of 10-4 in methylene chloride is added trifluoroacetic acid and anisole. The mixture is stirred for 1 hour at room temperature, concentrated and the residue washed with ether to give compound 10-5. (*J. Heterocyclic Chemistry* 1991, 1067).

Compound 10-6

To a suspension of 10-5 in methylene chloride, 1.5 eq of oxalyl chloride is slowly added at room temperature. After 30 minutes, the reaction mixture is concentrated to completely remove the oxalyl chloride. The resulting crude acid chloride is dissolved in THF and treated with an excess of tributyltin hydride at room temperature under stirring for 10 minutes. The reaction mixture is concentrated and the residue after washing with n-hexane gives 10-6 as a solid.

Compound 10-7

To a solution of aldehyde 10-6 in DMF is added sodium hydride (1.2 eq) at 0° C. The mixture is stirred for 10 minutes at room temperature. It is then poured into water and is extracted with methylene chloride. The organic layers are combined, washed with water and brine, dried with $MgSO_4$ and concentrated. The residue is purified by silica gel chromatography to give 10-7.

Compound 10-8

The compound 10-7 is reacted with with 1.1 eq of a boronic acid, 3 eq of sodium carbonate and 0.1 eq of tetrakis(triphenylphosphine) in toluene. The mixture is heated at reflux overnight. It is then cooled, diluted with ethyl acetate, and washed with saturated ammonium chloride solution. The organic layers are combined and washed three times with water and brine. The organic phase is dried ($MgSO_4$) and concentrated in vacuo. Purification via flash chromatography gives the desired product 10-8.

Compound 10-9

To a suspension of 10-6 in DMF is added a solution of sodium hydrosulfite hydrate in DMF and the mixture is stirred at room temperature for 30 minutes. It is then poured into water and the precipitate is collected and washed with water to give 10-9.

Compound 10-10

To a suspension of 10-9 in methylene chloride is added thionyl chloride. After stirring at room temperature for 10 minutes, the reaction is concentrated to obtain the crude chlorothiazine. To a solution of the crude chlorothiazine in DMF is added lithium chloride and the mixture is heated at 110° C. for few hours. Next the reaction is poured into water. The precipitate is collected and purified by silica gel chromatography to give 10-10.

Compound 10-11

The compound 10-10 is reacted with with 1.1 eq of a boronic acid, 3 eq of sodium carbonate and 0.1 eq of tetrakis(triphenylphosphine) in toluene. The mixture is heated at reflux overnight. It is then cooled, diluted with ethyl acetate, and washed with saturated ammonium chloride solution. The organic layers are combined and washed three times with water and brine. The organic phase is dried ($MgSO_4$) and concentrated in vacuo. Purification via flash chromatography gives the desired product 10-11.

Example 11
Synthesis of Representative Intermediate

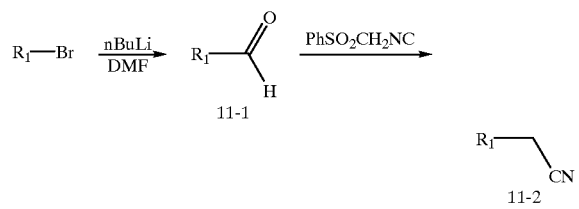

Compound 11-1

A solution of bromo compound $R_1$—Br (0.2 mol) in THF (400 mL) is cooled at −78° C. and is treated with BuLi (2.5M, 88 mL, 0.22 mol) slowly. The mixture is stirred for 20 minutes at −78° C. and DMF (20.1 mL, 0.24 mol) is added dropwise. The mixture is stirred for 10 minutes, the cooling bath removed, and the reaction is allowed to warm to room temperature. Water is added and the aqueous mixture is extracted with ethyl acetate, washed with brine, dried over $MgSO_4$ and concentrated in vacuo to give 11-1.

Compound 11-2

A solution of tosylmethyl isocyanide (15.4 g) in dimethoxyethane (50 mL) is added dropwise into a suspension of KOBu-t (10.16 g, 90 mmol) in dimethoxyethane (50 mL) at −60° C. After 10 minutes, a solution of aldehyde 11-1 (67 mmol) in dimethoxyethane (75 mL) is added dropwise. The mixture is stirred at −50° C. for 30 minutes and is quenched with methanol (200 mL). The mixture is refluxed for 1 hour, the solvent evaporated and the residue partitioned in ethyl acetate/water. The organic layer is washed with water, dried over $MgSO_4$, and filtered through a silica pad, eluting with ethyl acetate. The ethyl acetate is concentrated in vacuo giving compound 11-2 (62 mmol) as an oil.

Example 12
Synthesis of Representative Intermediate

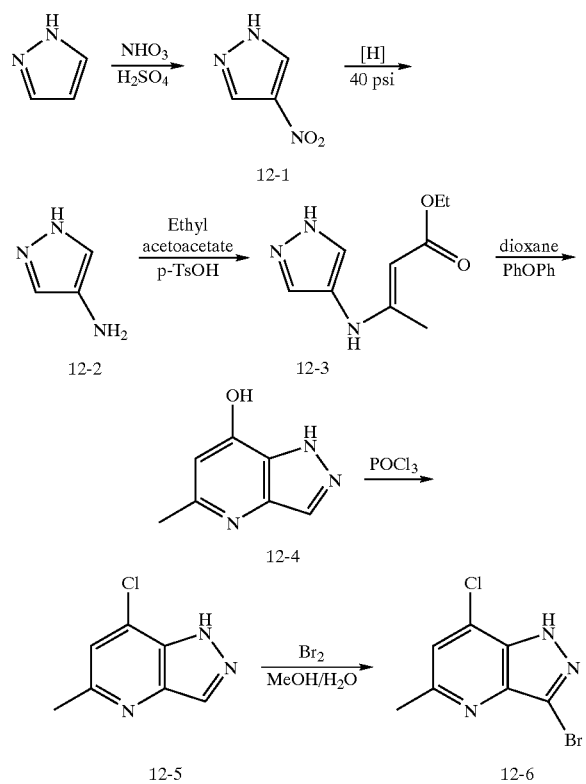

Compound 12-1

Pyrazole (Lancaster) (30.0 g, 441 mmol) was portionwise added to 220 mL of sulfuric acid (97%) in an ice-bath. The mixture was heated at 55° C. and 30 mL of nitric acid 70% (0.5 mol, 1.1 eq.) were added slowly. The reaction mixture was then stirred at 55° C. for 3 hours (reaction checked by TLC Ethylacetate/Hexane 1/1 pyrazole $R_f$=0.4, $I_2$ active, nitropyrazole Rf=0.6, UV active), cooled down, poured into 600 mL of ice-water and neutralized with 6N NaOH solution (pH=7). The product was then extracted with ethyl acetate (5×150 mL). The organic phases were combined, washed with water (100 mL), a brine solution (100 mL) and dried with sodium sulfate, filtered and concentrated by vacuum to yield the desired product 12-1 as a white solid (37.0 g, 326 mmol, 74%). GC/MS: m/z=113 (100%).

Compound 12-2

The 4-nitropyrazole 12-1 (15.0 g, 133 mmol) was added to a suspension of palladium on carbon 10% (7.0 g, 6.65 mmol, 5% mmol) in ethanol (100 mL). The mixture was shaken for 3 hours under hydrogen pressure (40 psi) at room temperature. The end of reaction checked by TLC (Ethylacetate/Hexane 1/1, 4-nitropyrazole $R_f$=0.6, UV active, 4-aminopyrazole $R_f$ 0.1, UV active). The catalyst was removed by filtration through a pad of Celite and the solvent was evaporated. The product 12-2 was obtained as a burgundy oil (10.5 g, 126 mmol, 95%), which was used in the following step without purification. GC/MS: m/z=83 (100%).

Compound 12-3

A solution of 4-aminopyrazole 12-2 (10.5 g, 126 mmol), ethylacetoacetate (18.0 g, 140 mmol, 1.05 eq.) and a catalytic amount of para-toluenesulfonic acid monohydrate (1.3 g, 6.65 mmol, 5%) in 100 mL of benzene was refluxed with a Dean-Stark trap for about 1 hour. The end of reaction was checked by TLC (Ethylacetate/Hexane 1/1, 4-aminopyrazole $R_f$=0.1, imine $R_f$=0.5, UV active, brown after overnight). Solvents were removed under vacuum and the imine was purified by running through a short silica chromatography column to give the desired product 12-3 as a tan solid (22.4 g, 125 mmol, 91%). GC/MS: m/z=195 (100%).

Compound 12-4

The imine 12-3 (7.03 g, 35.9 mmol) was added to a boiling solution of dioxane (30 mL) and diphenyl ether (30 mL). The mixture was heated until solid formed (5 min). The reaction mixture was heated for 2 more minutes. Heating was stopped. The end of the cyclization was checked by LC/MS (disappearance of 196). After cooling down at room temperature, 300 mL of diethyl ether was added and the reaction mixture was stirred for 15 minutes. The solid was rinsed with diethyl ether. The desired product 12-4 was obtained as a tan crystalline solid (5.09 g, 34.1 mmol, 95%). LC/MS: [M+H]'=150.

Compound 12-5

The cyclized compound 12-4 (4.58 g, 30.7 mmol) in phosphorus oxychloride (30 mL) was heated at 110° C. for 30 minutes. The end of the reaction was checked by LC/MS (disappearance of 150, appearance of 168). After cooling down at room temperature, the reaction mixture was poured on ice and the pH was adjusted with a 6N NaOH solution to pH=5. The solid was collected by filtration and the mother aqueous layer was extracted with ethyl acetate (3×250 mL). The above solid was dissolved in the combined organic phases, washed with a brine solution (1×250 mL) and dried with sodium sulfate, filtered and concentrated. The crude product was purified by running through a short silica gel chromatography column to give the desired product 12-5 as a pale yellow solid (4.50 g, 26.8 mmol, 87%). GC/MS: m/z=167 (100%);. LC/MS: [M+H]'=168.

Compound 12-6

The chloro compound 12-5 (600 mg, 3.58 mmol) was dissolved in a mixture of water/methanol (12 mL/12mL) in an ice-bath. A solution of bromine (629 mg, 3.94 mmol, 1.1 eq.) in a solution of $H_2O$/MeOH 1 mL/1 mL) was added dropwise to the cooled mixture. After 10 minutes, the solution was clearer and the LC/MS showed no more chloro compound. The reaction mixture was concentrated to remove the MeOH. The crude reaction mixture was extracted with ethyl acetate (3×50 mL). The organic phases were combined, washed with a brine solution (1×100 mL) and dried with sodium sulfate, filtered and concentrated by vacuum. The desired product 12-6 was obtained as a pale yellow solid. GC/MS: m/z=245, 247 (100%); LC/MS: [M+H]'=246, 248.

Example 13
CRF Receptor Binding Activity

The compounds of this invention may be evaluated for binding activity to the CRF receptor by a standard radioligand binding assay as generally described by DeSouza et al. (J. Neurosci. 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay is performed in 1.5 ml Eppendorf tubes using approximately $1\times10^6$ cells per tube stably transfected with human CRF receptors. Each tube receives about 0.1 ml of assay buffer (e.g., Dulbecco's phosphate buffered saline, 10 mM magnesium chloride, 20 $\mu$M bacitracin) with or without unlabeled sauvagine, urotensin I or CRF (final concentration, 1 $\mu$M) to determine nonspecific binding, 0.1 ml of [$^{125}$I] tyrosine-ovine CRF (final concentration ~200 pM or approximately the $K_D$ as determined by Scatchard analysis) and 0.1 ml of a membrane suspension of cells containing the CRF receptor. The mixture is incubated for 2 hours at 22° C. followed by the separation of the bound and free radioligand by centrifugation. Following two washes of the pellets, the tubes are cut just above the pellet and monitored in a gamma counter for radioactivity at approximately 80% efficiency. All radioligand binding data may be analyzed using the non-linear least-square curve-fitting program LIGAND of Munson and Rodbard (Anal. Biochem. 107:220, 1990).

Example 14
CRF-Stimulate Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (Synapse 1:572, 1987), with modifications to adapt the assay to whole cell preparations.

More specifically, the standard assay mixture may contain the following in a final volume of 0.5 ml: 2 mM L-glutamine, 20 mM HEPES, and 1 mM IMBX in DMEM buffer. In stimulation studies, whole cells with the transfected CRF receptors are plated in 24-well plates and incubated for 1 h at 37° C. with various concentrations of CRF-related and unrelated peptides in order to establish the pharmacological rank-order profile of the particular receptor subtype. Following the incubation, the media is aspirated, the wells rinsed once gently with fresh media, and the media aspirated. To determine the amount of intracellular cAMP, 300 $\mu$l of a solution of 95% ethanol and 20 mM aqueous hydrochloric acid is added to each well and the resulting suspensions are incubated at −20° C. for 16 to 18 hours. The solution is removed into 1.5 ml Eppendorf tubes and the wells washed with an additional 200 $\mu$l of ethanol/aqueous hydrochloric acid and pooled with the first fraction. The samples are lyophilized and then resuspended with 500 $\mu$l sodium acetate buffer. The measurement of cAMP in the samples is performed using a single antibody kit from Biomedical Technologies Inc. (Stoughton, Mass.). For the functional assessment of the compounds, a single concentration of CRF or related peptides causing 80% stimulation of cAMP production is incubated along with various concentrations of competing compounds ($10^{-12}$ to $10^{-6}$M).

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound having the following structure:

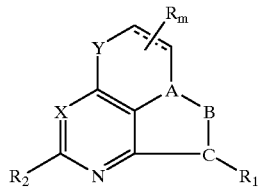

or a stereoisomer, prodrug or pharmaceutically acceptable salt thereof,
wherein:

X is nitrogen or $CR_3$;

Y is O or $S(O)_{0-2}$;

"- - -" represents an option double bond;

A and C are the same or different and independently nitrogen, carbon or CH;

B is nitrogen or $CR_4$;

with the provisos that at least one of A, B or C is nitrogen, A, B and C are not all nitrogen, and either A—B or B—C is a double bond;

R is an optional substituent which, at each occurrence, is independently alkyl, substituted alkyl, aryl, arylalkyl, alkylidenyl, heterocycle, heterocyclealkyl, alkoxy or —CO(alkoxy), wherein m is 0, 1, 2 or 3 and represents the number of R substituents;

$R_1$ is alkyl, substituted alkyl, aryl, substituted aryl, heteroaryl or substituted heteroaryl;

$R_2$ is hydrogen, alkyl, alkoxy or thioalkyl or haloalkyl;

$R_3$ is hydrogen, alkyl, halogen or haloalkyl; and $R_4$ is hydrogen, halogen, alkyl, alkoxy, thioalkyl or haloalkyl.

2. The compound of claim 1 wherein X is $CR_3$.
3. The compound of claim 1 wherein X is nitrogen.
4. The compound of claim 1 wherein Y is O.
5. The compound of claim 1 wherein Y is $S(O)_{0-2}$.
6. The compound of claim 5 wherein Y is S.
7. The compound of claim 5 wherien Y is SO.
8. The compound of claim 5 wherein Y is $SO_2$.
9. The compound of claim 1 wherein A is nitrogen, B is nitrogen, C is carbon and the double bond is between B and C.
10. The compound of claim 1 wherein A is carbon, B is nitrogen, C is nitrogen, and the double bond is between A and B.
11. The compound of claim 1 wherein A is carbon, B is $CR_4$, C is nitrogen, and the double bond is between A and B.
12. The compound of claim 1 wherein A is nitrogen, B is $CR_4$, C is carbon, and the double bond is between B and C.
13. The compound of claim 1 wherein $R_1$ is substituted aryl.
14. The compound of claim 13 wherein $R_1$ is substituted phenyl.
15. The compound of claim 1 wherein $R_2$ is hydrogen or alkyl.
16. The compound of claim 1 wherein $R_3$ is hydrogen, halogen, alkyl or haloalkyl.
17. The compound of claim 1 wherein $R_4$ is hydrogen or alkyl.
18. A composition comprising a compound of claim 1 in combination with a pharmaceutically acceptable carrier or diluent.
19. A method for treating a disorder manifesting hypersecretion of CRF in a warm-blooded animal, comprising administering to the animal an effective amount of the pharmaceutical composition of claim 18.
20. The method of claim 19 wherein the disorder is stroke.
21. The method of claim 19 wherein the disorder is depression.
22. The method of claim 19 wherein the disorder is anxiety.